(12) United States Patent
Viart et al.

(10) Patent No.: US 7,404,822 B2
(45) Date of Patent: Jul. 29, 2008

(54) SURGICAL INSTRUMENT

(75) Inventors: Guy Viart, Saint-Leger (FR); Eric Leroy, Saint Nicolas les Arras (FR); Jean-Yves Leroy, Campagne les Hesdin (FR); Arnaud Pommier, Raimbeaucourt (FR)

(73) Assignee: Orthotec, LLC, Beverly Hills, CA (US)

( * ) Notice: Subject to any disclaimer, the term of this patent is extended or adjusted under 35 U.S.C. 154(b) by 0 days.

(21) Appl. No.: 10/494,050

(22) PCT Filed: Oct. 23, 2002

(86) PCT No.: PCT/FR02/03628

§ 371 (c)(1),
(2), (4) Date: Apr. 29, 2004

(87) PCT Pub. No.: WO03/037193

PCT Pub. Date: May 8, 2003

(65) Prior Publication Data
US 2004/0254604 A1    Dec. 16, 2004

(30) Foreign Application Priority Data
Oct. 30, 2001    (FR) .................................. 01 14005

(51) Int. Cl.
*A61B 17/28* (2006.01)
*A61B 17/42* (2006.01)
*A61B 17/44* (2006.01)
(52) U.S. Cl. .................... 606/208; 606/205; 606/210
(58) Field of Classification Search ................. 606/205, 606/206, 207, 208, 210
See application file for complete search history.

(56) References Cited

U.S. PATENT DOCUMENTS

| | | | | |
|---|---|---|---|---|
| 2,544,197 | A | * | 3/1951 | Vosbikian et al. ............. 30/262 |
| 2,652,832 | A |   | 9/1953 | Castroviejo |
| 4,462,404 | A |   | 7/1984 | Schwarz |
| 4,722,339 | A | * | 2/1988 | Dreier et al. ................ 606/208 |
| 4,961,742 | A | * | 10/1990 | Torre .......................... 606/147 |
| 5,104,397 | A |   | 4/1992 | Santangelo et al. |
| 5,314,424 | A | * | 5/1994 | Nicholas ..................... 606/41 |
| 5,425,743 | A | * | 6/1995 | Nicholas ..................... 606/208 |
| 5,653,729 | A | * | 8/1997 | Chappuis et al. ............ 606/207 |
| 5,730,740 | A | * | 3/1998 | Wales et al. ................... 606/1 |
| 5,752,960 | A | * | 5/1998 | Nallakrishnan ............. 606/107 |
| 6,139,563 | A | * | 10/2000 | Cosgrove et al. ............ 606/205 |
| 6,202,517 | B1 | * | 3/2001 | Dolan ........................ 81/427 |
| 6,446,344 | B1 | * | 9/2002 | Gontar ........................ 30/262 |

FOREIGN PATENT DOCUMENTS

DE    198 41 249    5/2000
EP    0 392 548     10/1990

* cited by examiner

*Primary Examiner*—Michael J. Hayes
*Assistant Examiner*—Michael G. Mendoza
(74) *Attorney, Agent, or Firm*—Blakely Sokoloff Taylor & Zafman

(57) ABSTRACT

A surgical instrument includes: grip handles (2, 3) which are articulated to each other around a fulcrum pin (4) so that the jaws can be moved from an open position to a closed position; and connecting elements (5) which can be used to: (i) lock the handles (2, 3) in a determined, constant position when a first force is exerted on the handles; and (ii) unlock the handles (2, 3) when a second force is exerted on same.

7 Claims, 5 Drawing Sheets

SURGICAL INSTRUMENT

The present invention relates to a surgical instrument and more particularly to connection means permitting, under the effect of different pressure forces, the locking and unlocking of the handles.

There are known surgical instruments of this type which comprise handles articulated to each other about a pivotal axis, for movement of the jaws from an open position to a closed position, and locking means and/or unlocking means for said handles.

The surgical instrument according to the present invention comprises handles articulated to each other about a pivotal axis for the movement of jaws, from an open position to a closed position, and connection means which permit on the one hand under the effect of a first pressure on the handles, locking these latter in a predetermined and constant position and, on the other hand, under the effect of a second pressure on said handles, unlocking these latter.

The surgical instrument according to the present invention comprises connection means which are constituted, on the first handle, by an ear permitting the securement of a hook and in the second handle, of an open recess in which is secured catch.

The surgical instrument according to the present invention comprises a hook which comprises a hooking portion and resilient return portion, which is constituted by a spring to place said hook in a same and single position when the surgical instrument is in the unlocked position.

The surgical instrument according to the present invention comprises an ear which is pierced with a hole to receive an axle permitting the securement of the hook on the handle.

The surgical instrument according to the present invention comprises an open recess, which is provided to pass through from side to side the thickness of the handle such that the hooking region of the catch, which is constituted by at least one tooth, will be directed in the direction of the hook secured to the handle.

The surgical instrument according to the present invention comprises a catch which comprises a tooth formed by a recess, which is delimited by a first inclined surface providing an access ramp to the interior of said tooth and by another inclined surface constituting an exit ramp from said tooth.

The surgical instrument according to the present invention comprises a catch whose thickness is formed by a profile with a curved surface connecting the two first inclined surfaces.

The surgical instrument according to the present invention comprises inclined surfaces which are positioned in separate and parallel planes so as to facilitate the sliding of the hooking portion of the hook.

The surgical instrument according to the present invention comprises a catch which is positioned and fixed within the open recess, such that the bottom of the recess of the tooth will be located on the one hand within said recess and on the other hand at the same level as the securement axle of the hook on the handle.

The description which follows with respect to the accompanying drawings, given by way of non-limiting example, will permit better understanding of the invention, the characteristic which it presents and the advantages that it is adapted to provide:

Figure 1:
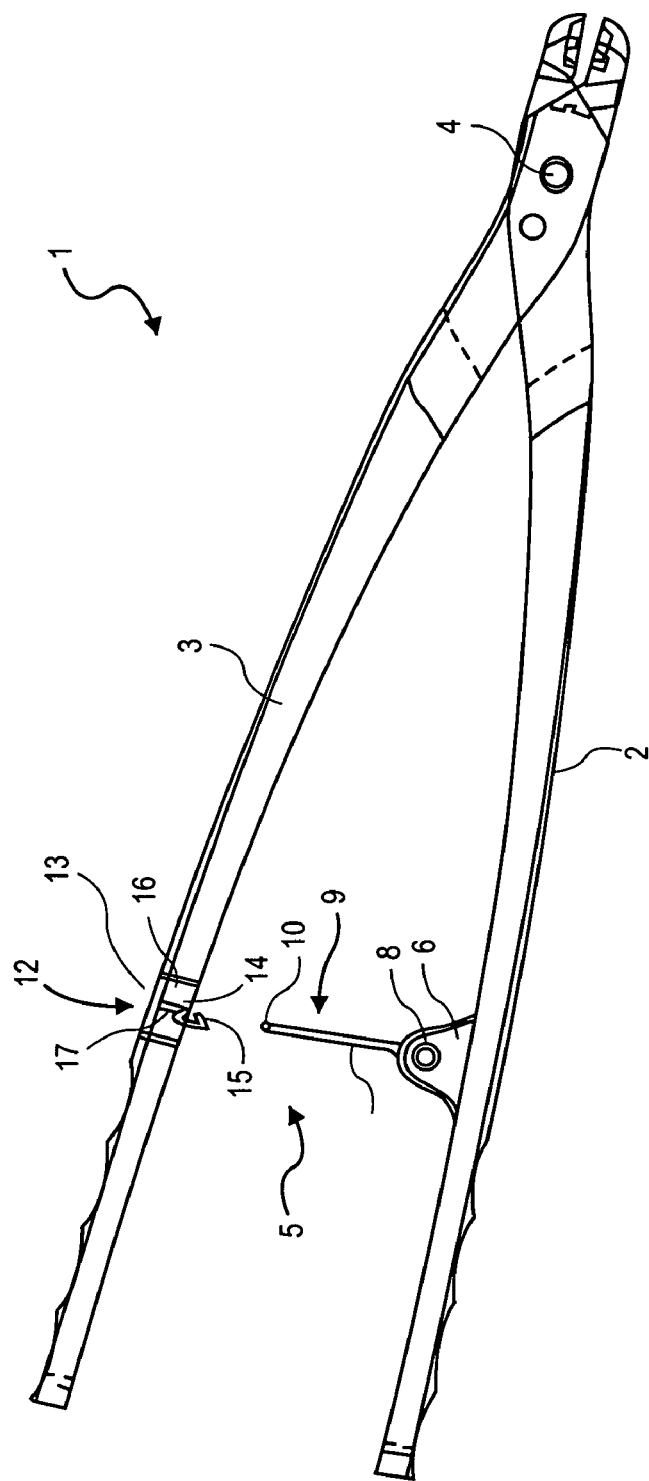
FIG. 1 is a view showing the connection means of the handles in the unlocked position of a surgical instrument according to the present invention.

There is shown in FIG. 1 a surgical instrument 1 of the pliers type comprising two handles 2, 3 which are articulated to each other about a pivotal axis 4 for closing and/or opening the jaws (not shown).

The jaws can be present in any form depending on their function, which can be for example cutting or gripping.

The handles 2 and 3 of the surgical instrument 1 comprise, opposite the pivotal axis 4, connection means 5 which permit, as a function of the force applied by the surgeon, on said handles, either to interconnect them, or to free them from each other.

The connection means 5 are constituted, on the first handle 2 of the surgical instrument 1 and in the direction of the second handle 3, by an ear 6 which is pierced by a hole 7 to receive an axle 8 permitting the securement of a hook 9.

The hook 9 comprises a hooking portion 10 and a resilient return portion which is constituted by a spring 11 to place said hook 9 in a same and single position when the surgical instrument 1 is in the open position.

The connection means 5 are constituted, in the second handle 3, by an open recess 12 in which is secured a catch 13.

The open recess 12 is provided to pass through from side to side of the thickness of the handle 3 such that the hooking region of the catch 13, which is constituted by at least one tooth 14, will be directed in the direction of the hook 9 secured to the handle 2.

Figure 2:
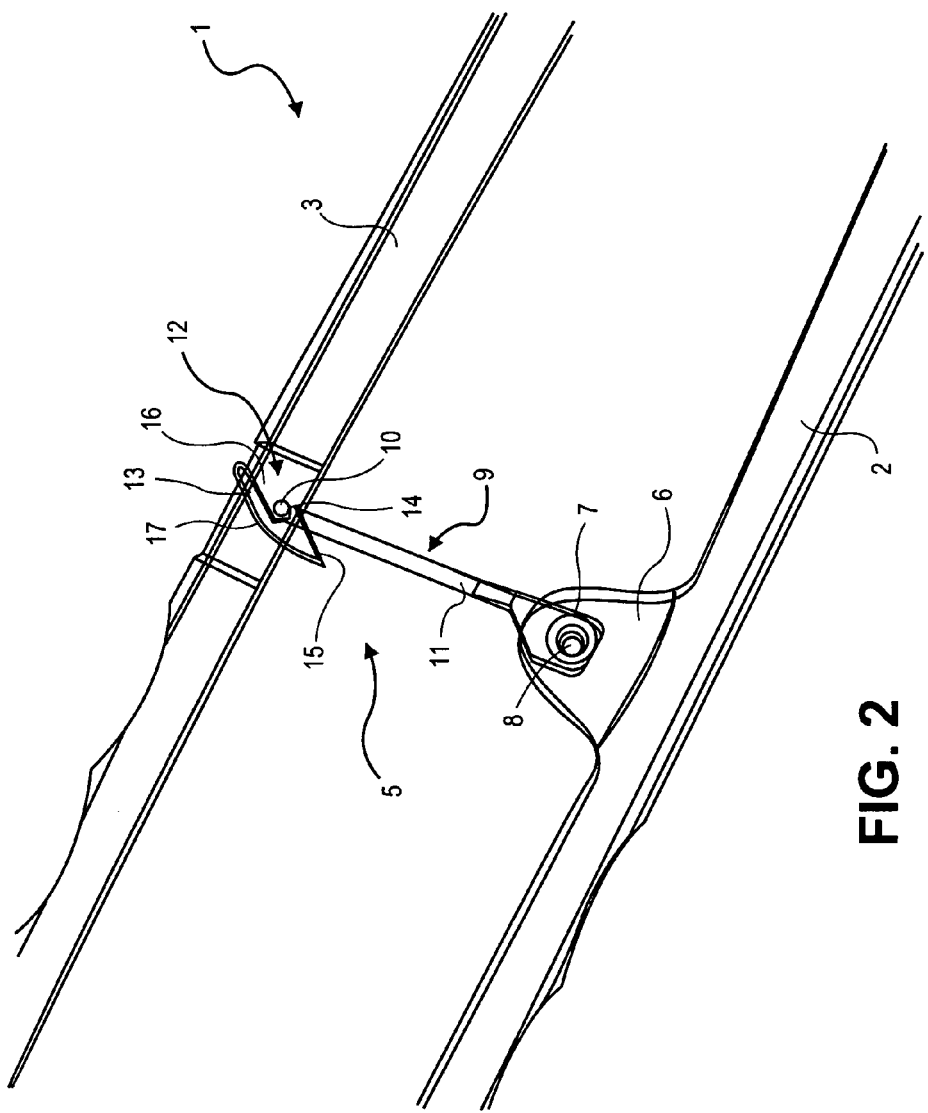
FIG. 2 is a view showing the connection means for the handles in the locked position of a surgical instrument according to the present invention.

It will be seen that the surgical instrument 1 is in the locked position when the hooking portion 10 of the hook 9 secured to the first handle 2 coacts with the recess of the tooth 14 of the catch 13, fixed on the second leg 3 (FIG. 2).

The locked position of the surgical instrument 1 is achieved when the surgeon exerts first pressure on the handles 2 and 3 so as to bring them toward each other.

During this pressure, it will be seen that the hooking portion 10 of the hook 9 slides on the inclined surface 15 of the catch 3 until it comes into coaction with the bottom of the recess of the tooth 14.

The locking of the surgical instrument 1 is finalized when the surgeon releases the pressure. This locked position is maintained until the surgeon exerts a new pressure on the handles 2 and 3 of the surgical instrument 1.

Figure 3:
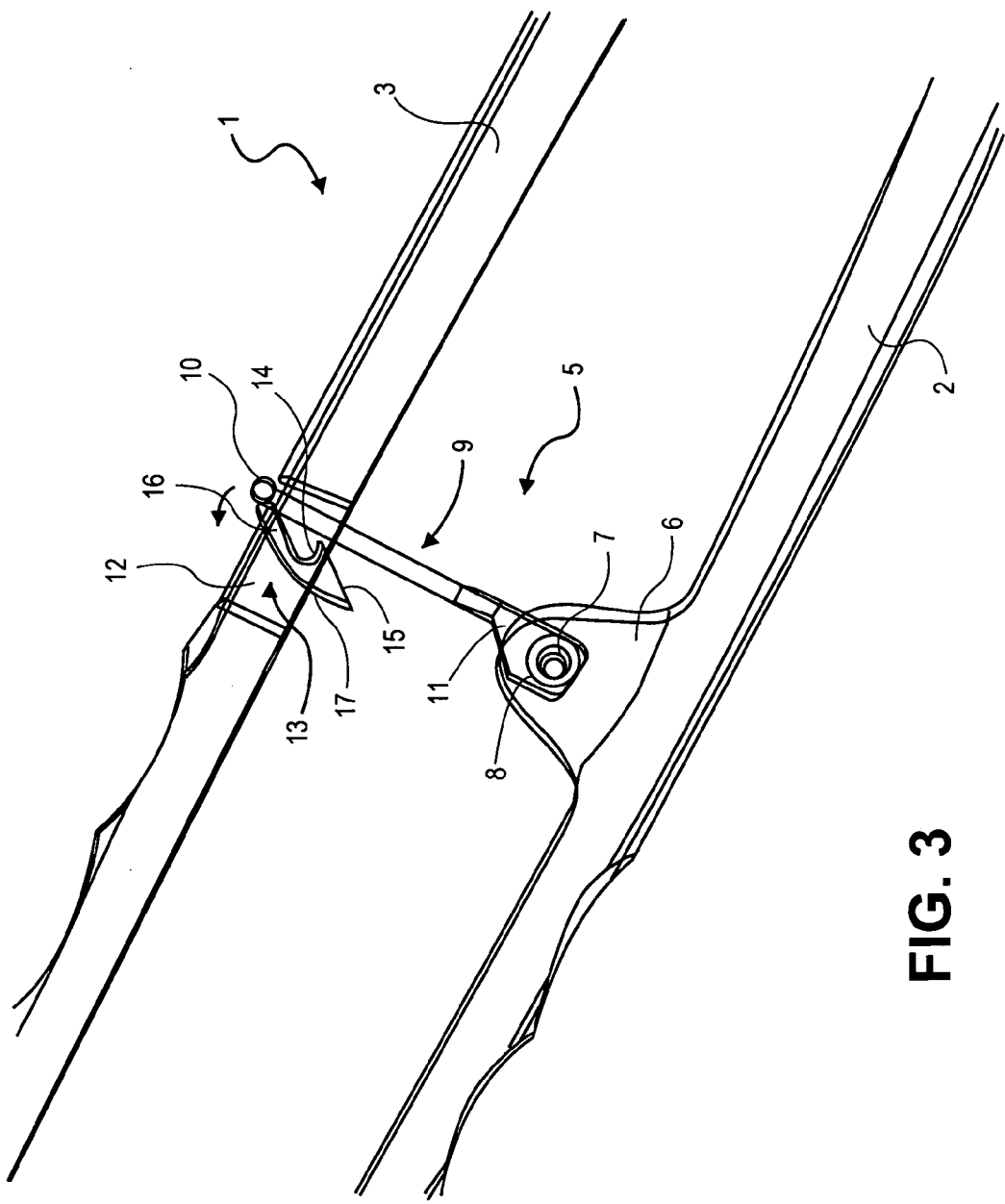
FIGS. 3 to 5 are views showing the movements of the connection means permitting the unlocking of the handles of a surgical instrument according to the present invention.
Figure 4:
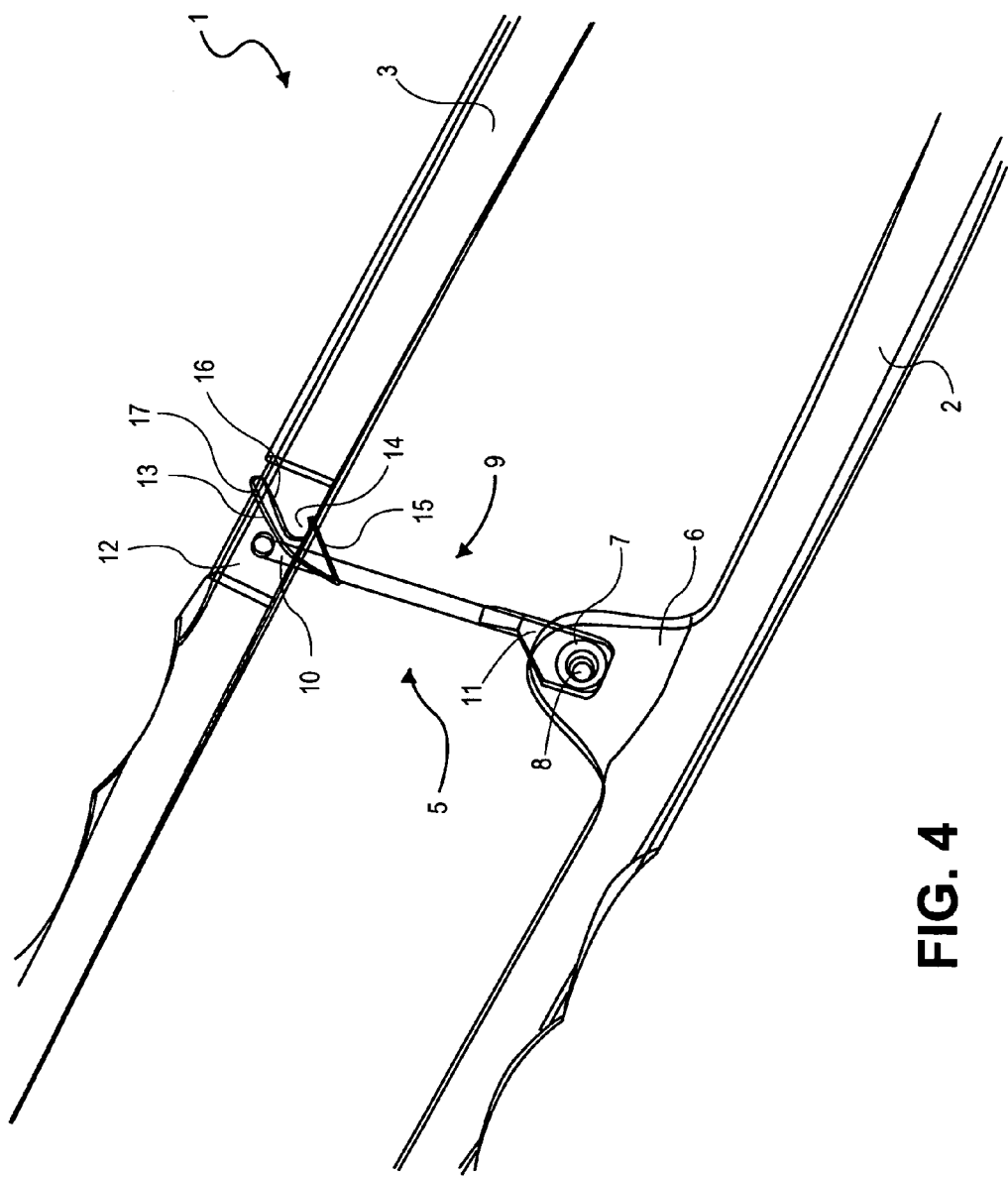
Figure 5:
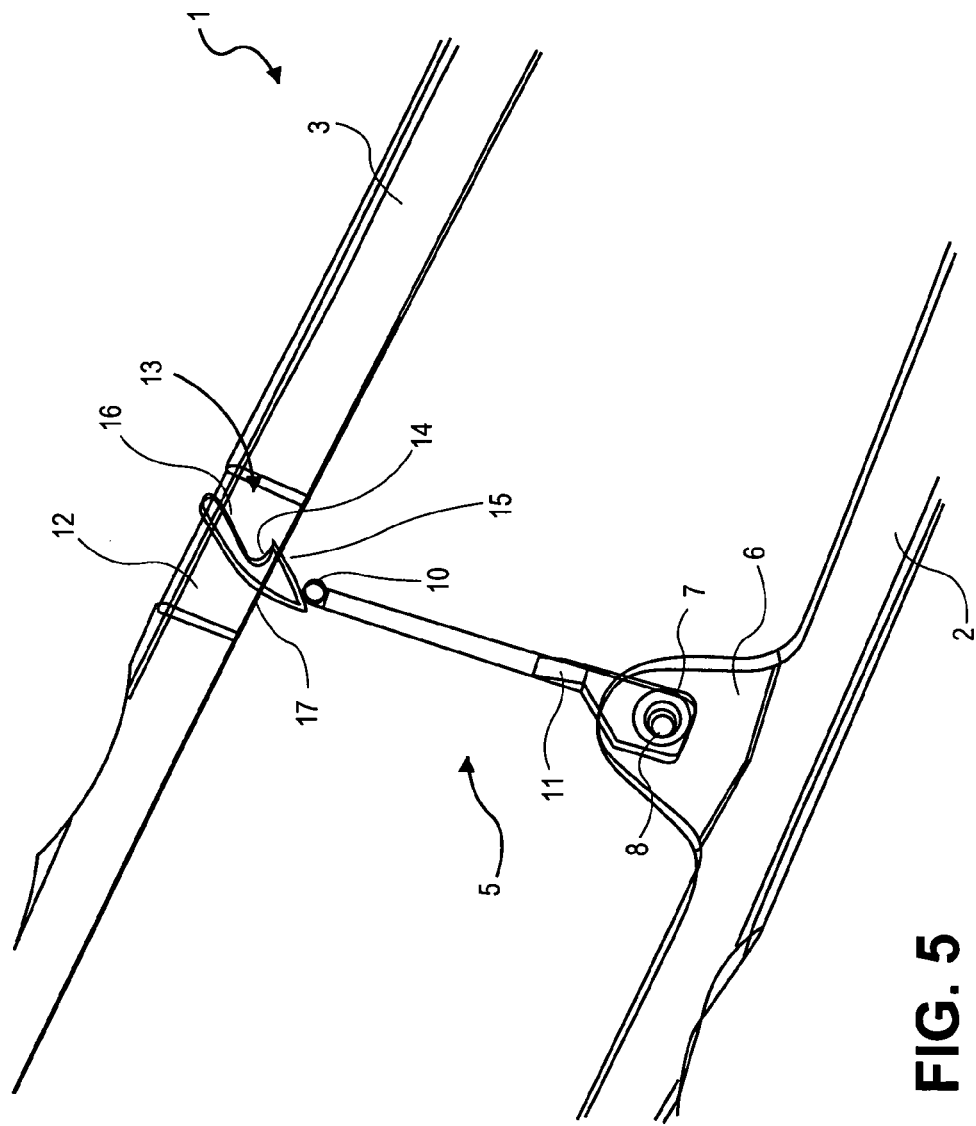

In FIGS. 3 to 5 there is shown the movement of the hook 9 relative to the fixed catch 13 when the surgeon exerts a second pressure on the legs 2 and 3 of the surgical instrument 1.

The unlocking of the surgical instrument 1 takes place when the surgeon exerts a second pressure which is directed in the same direction as that permitting locking.

This second pressure consists in bringing the handles 2 and 3 a bit closer to each other to move the hooking portion 10 of the hook 9 out of the recess of the tooth 14 (FIG. 3).

The continuation of the second pressure by the surgeon permits causing the hooking portion 10 of the hook 9 to slide over the inclined surface 16 until it passes automatically from the other side to come into sliding contact with the curved profile 17 of the latch 3 (FIGS. 3 and 4).

The surgeon then relaxes the pressure, which results in a spacing apart of the handles 2 and 3 of the surgical instrument 1 and the continued sliding of the hooking portion 10 over the curved profile surface 17 (FIG. 4).

The complete relaxation of the pressure permits, under the influence of a return spring (not shown), a total opening of the surgical instrument 1 so as to position the hooking portion 10 of the hook 9 at the beginning of the inclined surface 15 of the catch 13 (FIG. 5).

It will be seen that the connection means 5 are adaptable to all surgical instruments comprising handles articulated about a pivotal axis.

It will be noted that the connection means 5 permit manipulating a surgical instrument with a single hand, by a single, rapid and repetitive movement, to lock and unlock the handles.

It should be understood that the preceding description was given only by way of example and that it in no way limits the scope of the invention, from which no departure will be made by replacing the details of execution described, by any other equivalent.

The invention claimed is:

1. Surgical instrument comprising handles (2, 3) articulated about a pivotal axis (4) for moving jaws, from an open position to a closed position, comprising connection means (5) which permit on the one hand, under a first pressure on the handles (2, 3) locking the handles in a predetermined and constant position, and on the other hand, under the influence of a second pressure on said handles (2, 3) unlocking the handles wherein an open recess (12) is provided to pass through from side to side of a thickness of the second handle (3) such that a hooking region of a catch (13), which is constituted by at least one tooth (14), is directed in a direction of a hook (9) secured to the first handle (2), and wherein the connection means (5) are constituted on the first handle (2) by an ear (6) permitting securement of the hook (9), and on the second handle (3), by the open recess (12) in which is secured the catch (13).

2. Surgical instrument according to claim 1, wherein the hook (9) comprises a hooking portion (10) and a resilient return portion which is constituted by a spring (11) to place said hook (9) in a same and single position when the handles are in the unlocked position.

3. Surgical instrument according to claim 1, wherein the ear (6) is pierced by a hole (7) to receive an axle (8) permitting the securement of the hook (9) on the first handle (2).

4. Surgical instrument according to claim 3, wherein the catch (13) comprises the at least one tooth (14) formed by a hollow which is delimited by a first inclined surface (15) forming an access ramp within said tooth, and by another inclined surface (16) constituting an access ramp from said tooth.

5. Surgical instrument according to claim 4, wherein a thickness of the catch (13) is formed by a surface (17) with a curved profile connecting the inclined surfaces (15 and 16).

6. Surgical instrument according to claim 4, wherein the inclined surfaces (15, 16) are positioned in separate and parallel planes so as to facilitate sliding of a hooking portion (10) of the hook (9).

7. Surgical instrument according to claim 2, wherein the catch (13) is positioned and fixed within the opening recess (12) such that a bottom of a recess of the at least one tooth (14) is located within said recess (12) at a same level as a securement axle (8) of the hook (9) on the first handle (2).

* * * * *